United States Patent [19]

Schlecker et al.

[11] Patent Number: 5,654,310

[45] Date of Patent: Aug. 5, 1997

[54] TRIAZOLOPYRIMIDONES THEIR PREPARATION AND USE

[75] Inventors: Rainer Schlecker, Bissersheim; Hans-Joerg Treiber, Bruehl; Berthold Behl, Ludwigshafen; Hans Peter Hofmann, Limburgerhof, all of Germany

[73] Assignee: BASF Aktiengesellschaft, Ludwigshafen, Germany

[21] Appl. No.: 446,838

[22] Filed: Jun. 1, 1995

[30] Foreign Application Priority Data

Dec. 10, 1992 [DE] Germany ............... 42 41 562.4

[51] Int. Cl.⁶ .................. A61K 31/505; C07D 487/04
[52] U.S. Cl. .................. 514/267; 514/257; 548/247; 548/251
[58] Field of Search ............. 544/251, 247, 544/257, 267

[56] References Cited

U.S. PATENT DOCUMENTS 4,053,600 10/1977 Hardtmann et al. .
4,128,644 12/1978 Vogt .
4,463,007 7/1984 Schlecker et al. .
5,153,196 10/1992 McQuaid et al. .

FOREIGN PATENT DOCUMENTS 217 748   4/1987   European Pat. Off. .

*Primary Examiner*—Patricia L. Morris
*Attorney, Agent, or Firm*—Keil & Weinkauf

[57] ABSTRACT

Triazolopyrimidines of the formula

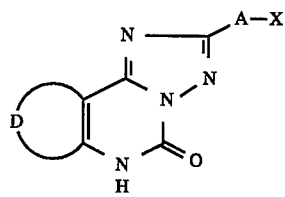

where A, D and X have the meanings stated in the description, and their preparation are described. The novel compounds are suitable for controlling diseases.

6 Claims, No Drawings

TRIAZOLOPYRIMIDONES THEIR PREPARATION AND USE

The present invention relates to novel triazolopyrimidones, a process for their preparation and their use for controlling diseases.

Pyrazolo- and triazoloquinazolines with antiallergic and anti-inflammatory properties have been disclosed (EP 80 176, U.S. Pat. No. 4,053,600, U.S. Pat. No. 4,128,644). Also known are pyrazoloquinazolines which are furthermore suitable for the treatment of thrombosis and neurological disorders (U.S. Pat. No. 5,153,196).

We have now found that triazolopyrimidones of the formula I

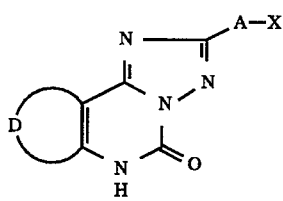

where

A is a direct linkage or a $C_{1-3}$-alkylene chain,

D is a $C_{3-6}$-alkylene chain which can be interrupted by a nitrogen, sulfur or oxygen atom and/or can carry a fused-on aromatic or aliphatic ring, X is a carboxyl group which may be in the form of its salt with a physiologically tolerated amine cation or metal cation; the radical

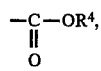

where $R^4$ is a $C_{1-8}$-alkyl radical, a cycloalkyl group with 3 to 8 carbon atoms in the ring, a benzyl radical, one of the radicals $-(CH_2)_n-O-R^5$ or

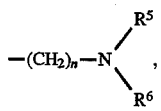

where n is the number 2, 3 or 4 and $R^5$ and $R^6$ are each a $C_{1-3}$-alkyl group; a hydroxy-$C_{1-4}$-alkyl, cyano-$C_{1-4}$-alkyl, tetrazolyl, carbonylaminotetrazolyl, $C_{1-4}$-alkylcarbonyl or an unsubstituted or substituted carbamoyl group, have a different spectrum of actions.

Examples of substituents A–X which may be mentioned are the radicals of the following compounds:

formic acid, acetic acid, 2-propionic acid, 3-propionic acid, 4-butyric acid, 3-butyric acid, 2-butyric acid, 5-valeric acid, 4-valeric acid, 3-valeric acid, 2-valeric acid and their methyl, ethyl, propyl, isopropyl, butyl, pentyl, hexyl, heptyl, cyclobutyl, cyclopropyl, cyclopentyl, cyclohexyl, cycloheptyl and cyclooctyl esters or their amides such as the methylamides, dimethylamides, ethylamides, diethylamides, propylamides, butylamides, benzylamides; hydroxymethane, 1-hydroxy-ethane, 2-hydroxyethane, 1-hydroxypropane, 2-hydroxypropane, 3-hydroxypropane, 1-hydroxypropane, 2-hydroxypropane, 3-hydroxypropane, 1-hydroxybutane, 2-hydroxybutane, 3-hydroxybutane, 4-hydroxybutane, hydroxypentane, hydroxyheptane; methoxymethane, methoxyethane, methoxypropane, methoxybutane, ethoxymethane, ethoxypropane, ethoxybutane. Oxomethane, 1-oxoethane, 2-oxoethane, 1-oxopropane, 2-oxopropane, 3-oxopropane, 1-oxobutane, 2-oxobutane, 3-oxobutane, 4-oxobutane, 1-oxopentane, 2-oxopentane, 3-oxopentane, 4-oxopentane; cyanomethane, cyanoethane, 1-cyanopropane, 2-cyanopropane, 3-cyanopropane, 1-cyanobutane, 2-cyanobutane, 3-cyanobutane, 4-cyanobutane.

The following radicals may be mentioned specifically for D:

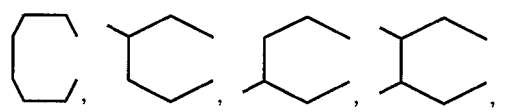

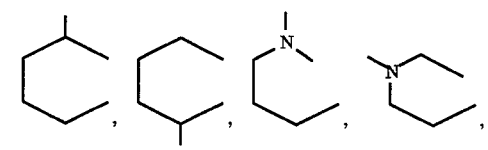

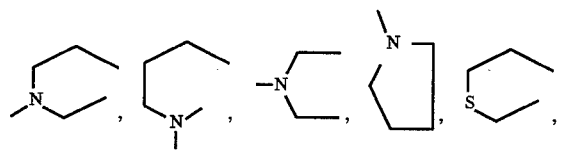

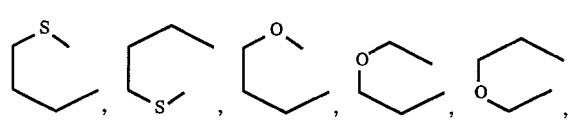

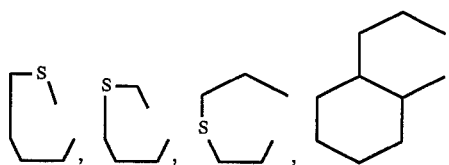

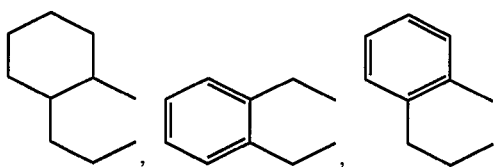

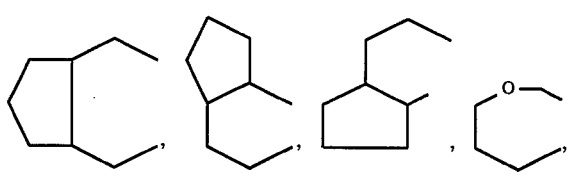

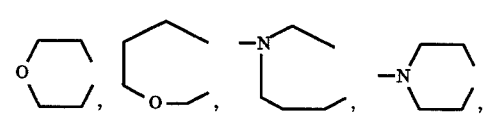

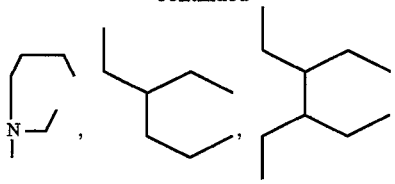

The compounds of the formula I can be prepared by an intramolecular condensation of a hydrazinopyrimidine of the formula II

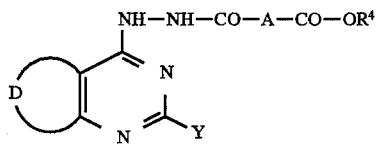

where A, D, X and $R^4$ have the meanings stated for formula I, and Y is a hydroxyl group or a bromine or chlorine atom, preferably in the presence of a dehydrating agent, in particular of phosphorus oxychloride, polyphosphoric acid or acetic acid, in the presence or absence of an inert solvent, such as toluene, chlorobenzene, xylene or excess acetic acid, at from 50° to 150° C., preferably at the reflux temperature of the reaction mixture.

The esters obtained in this way can subsequently be hydrolyzed and the free acids can be converted with an amine or a metal cation into physiologically tolerated salts. The free acids can also be reduced to the hydroxyalkyl compounds (X=hydroxyalkyl) or converted by conventional methods into the nitriles, tetrazolamino and carbamoyl compounds.

The compounds of the formula I where X is a carboxyl group are prepared by hydrolyzing the corresponding esters, preferably under alkaline conditions, for example in the presence of an alkali metal hydroxide or sodium bicarbonate, in a solvent such as water, a lower alcohol, tetrahydrofuran or mixtures thereof. The organic acids obtained in this way are converted where appropriate into a physiologically tolerated amine or metal salt. By this are meant, in particular, salts of the alkali metals such as sodium and potassium, of the alkaline earth metals such as calcium, other metals such as aluminum, and salts or organic bases such as morpholine, piperidine, mono-, di- and triethanolamino or tris(hydroxymethyl)aminomethane, which are generally known to the skilled worker.

Carboxylic acids of the formula I can furthermore be prepared by hydrogenolysis of the corresponding benzyl esters by conventional methods as described, for example, in Houben-Weyl, Vol. IV/1c pages 381 et seq. The reaction takes place in the presence of a catalyst such as platinum, palladium or nickel, expediently on a support, especially carbon, in a solvent such as a lower alcohol, especially methanol, acetic acid or a dialkylformamide, especially dimethylformamide, at from 0° C. to the boiling point of the solvent, and preferably under only slightly elevated pressure.

Amides of the formula I where X is a carbamoyl group are obtained by reacting the esters with ammonia or amine in the presence of a solvent such as water, a lower alcohol, an aqueous alcoholic solution or dialkylformamide at from 0° C. to the reflux temperature of the system.

Treatment of primary amides with a dehydrating agent such as phosphorus pentoxide, phosphorus oxychloride or thionyl chloride results in the nitriles of the compounds of the formula I where X is a cyano group. The reaction is generally carried out with an excess of the dehydrating agent at the reflux temperature of the mixture. The reaction may, where appropriate, be carried out in the presence of an inert solvent such as benzene or ethylene chloride.

Compounds of the formula I where X is a tetrazolyl radical are synthesized by conventional methods as described, for example, in Synth. 1973, 80, by reacting the amides with hydrazoic acid or one of its salts, for example with alkali metal or alkaline earth metal azides, in the presence or absence of Lewis acids such as aluminum chloride and tin chloride or of ammonium chloride. The combination of sodium azide with ammonium chloride is preferred. The reaction is generally carried out in the presence of an inert solvent such as benzene, tetrahydrofuran or dimethylformamide at from room temperature to 150° C. The tetrazolyl compounds are strong acids and can be converted in a conventional way into a salt with a physiologically tolerated amine or metal cation.

Reduction of carboxylic acids, especially of an ester of a compound of the formula I, by known processes, for example using a complex metal hydride such as lithium borohydride, in the presence of an ether such as tetrahydrofuran as solvent, provides the hydroxymethyl compounds of the formula I (X=CH$_2$OH). The reduction is preferably carried out at the boiling point of the reaction mixture.

Compounds of the formula I with a carbonylaminotetrazoyl [sic] radical for X (X=CO—NH—CHN$_4$) can be obtained by conventional methods by condensing the appropriate carboxylic acid with 5-aminotetrazole of the formula III

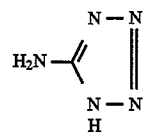

The reaction is, as a rule, carried out in an inert solvent such as methylene chloride, dioxane, tetrahydrofuran or dimethylformamide, preferably in the presence of a condensing agent known from peptide chemistry, such as N,N'-carbonyldiimidazole or N,N'-dicyclohexylcarbodiimide, at from 20° to 120° C.

Compounds of the formula I where X is an unsubstituted or substituted carbamoyl radical can also be prepared from the corresponding acids in a similar way.

The starting compounds of the formula II are prepared in a conventional way by condensing a hydrazinopyridone of the formula IV with an acyl halide of the formula V

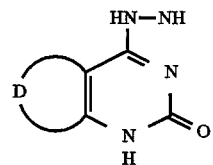

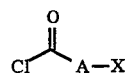

or a corresponding ester.

When an acyl halide, preferably a chloride, is used, the reaction expediently takes place at from −30° C. to 70° C., preferably at room temperature, in an inert solvent such as dimethylformamide, dioxane, tetrahydrofuran or methylene chloride. The reaction is preferably carried out in the presence of tertiary organic bases such as triethylamine or pyridine.

The reaction of IV with esters can be carried out with or without solvents such as toluene, chlorobenzene or diphenyl ether, at from about 20° C. to the reflux temperature of the mixture. The esters of the formula I can be transesterified by conventional processes as described, for example, in Houben-Weyl, Vol 8, pages 526–528 with alcohols to give esters with a different radical $R^4$.

Compounds of the formula I where X is cyano, tetrazolyl or hydroxymethyl and is bonded directly to the heterocycle are preferably synthesized from the corresponding acid by the processes described above.

Another process for preparing starting compounds of the formula II comprises reacting a hydrazine of the formula VI with a pyrimidine of the formula VII where X is a nucleofugic leaving group.

$H_2NNHCOAX$                  VI

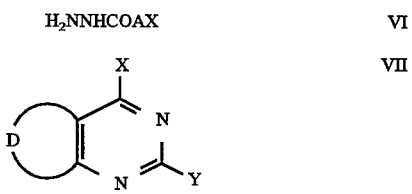

VII

The reaction is carried out at from 0° C. to 50° C. in an inert solvent such as ethanol, methylene chloride, toluene, tetrahydrofuran or dimethylformamide, preferably with an excess of VI.

The compounds of the formula IV are expediently prepared by condensing a compound of the formula VII with hydrazine. The process is carried out in a conventional way, ie. in general from –20° C. to 50° C. in an inert solvent such as dioxane, tetrahydrofuran, methylene chloride or dimethylformamide.

The compounds of the formula VII where X and Y are each chlorine or bromine can be prepared by conventional methods by reacting the corresponding pyrimidine-2,4-diones with phosphorus oxychloride or oxybromide. These reactions are, as is the synthesis of the pyrimidine diones, described in The Chemistry of Het. Compounds, The Pyrimidines, Wiley 1962, New York.

The compounds according to the invention are suitable for the treatment of disorders of the central nervous system. These include, in particular, disorders attributable to an acute or chronic disturbance of the blood supply and/or of cellular metabolism of the central nervous system, such as ischemic cerebral insults, vascular encephalopathies and the resulting dementias, epilepsies, Parkinson's disease, depression, migraine and traumatic lesions of the brain and the spinal cord.

The pharmacological activity of the compounds I according to the invention was investigated on isolated membrane material from rat cerebra. For this, the membrane material was treated in the presence of the compounds according to the invention with the radio-labeled substances $^3$H-2-amino-3-hydroxy-5-methyl-4-isoxazolepropionic acid ($^3$H-AMPA) and $^3$H-5,7-dichlorocyanuric [sic] acid, which bind to specific receptors (AMPA and NMDA (N-methyl-D-aspartate) receptors respectively). Subsequently the radioactivity in the treated membranes was measured by scintillation counting. It was possible from the bound radioactivity to determine the amounts of bound 3H AMPa and $^3$H-5,7-dichlorokyanurenic acid, or the amounts of each of these radiolabeled substances displaced. The dissociation constant $K_I$ (I=inhibitor) resulting from this is a measure of the displacing action of the agent according to the invention and was determined by iterative non-linear regression analysis using the Statistical Analysis System (SAS) on an IBM computer similar to the "Ligand" program of P. J. Munson and D. Rodbard (Analytical Biochem. 107, 220 (1980), Ligand: Versatile Computerized Approach for Characterization of Ligand Binding Systems).

The following in vitro investigations were carried out:
1. Binding of $^3$H-2-amino-3-hydroxy-5-methyl-4-isoxazolepropionic acid ($^3$H-AMPA).

To prepare the membrane material, freshly removed rat cerebra were homogenized together with about 15 times the volume of a buffer solution A composed of 30 mM α,α,α-tris(hydroxymethyl)methylamine hydrochloride (TRIS-HCl) and 0.5 mM ethylenediaminetetraacetic acid (EDTA), pH 7.4, using an Ultra-TURRAX. The suspension was centrifuged at 48,000 g for 20 min. After removal of the supernatant liquid, the protein-containing membrane material present in the pellet was washed three times by suspension in buffer solution A and subsequent centrifugation at 48,000 g for 20 minutes each time. The membrane material was then suspended in 15 times the volume of buffer solution A and incubated at 37° C. for 30 minutes. Subsequently the protein material was washed twice by centrifugation and suspension and was stored at –70° C. until used.

For the binding test, the protein material was thawed at 37° C. and washed twice by centrifugation at 48,000 g (20 min) and subsequent suspension in a buffer solution B composed of 50 mM TRIS-HCl, 0.1M potassium thiocyanate and 2.5 mM calcium chloride, pH 7.1. Subsequently, 0.25 mg of membrane material, 0.1 µCi of $^3$H-AMPA (60 Ci/mmol) and compound I were dissolved in 1 ml of buffer solution B and incubated on ice for 60 minutes. The incubated solution was filtered through a CF/B filter (supplied by Whatman) which had previously been treated for at least 2 hours with a 0.5% strength aqueous solution of polyethyleneimine. The filtrate [sic] was subsequently washed with 5 ml of cold buffer solution B in order to separate bound and free $^3$H-AMPA from one another. After measurement of the radioactivity of the bound $^3$H-AMPA in the membrane material by scintillation counting, the $K_I$ was determined by regression analysis of the displacement plots.

The results in this experiment were as follows:

| Substance of Example No. | AMPA binding $K_I$ [µm] |
|---|---|
| 3 | 1.5 |
| 10 | 1.7 |
| 11 | 1.0 |
| 21 | 1.7 |

Binding of $^3$H-5,7-dichlorokynurenic acid

To prepare the membrane material, freshly removed rat cerebra were homogenized together with about 10 times the volume of a buffer solution A' composed of 50 mM TRIS-HCl and 10 mM EDTA, pH 7.4. The suspension was centrifuged at 48,000 g for 20 minutes. After removal of the supernatant liquid, the membrane material contained in the pellet was washed twice by suspension in buffer solution A' and subsequent centrifugation of 20 minutes each time and suspension. After resuspension of the membranes in buffer solution A' and freezing in liquid nitrogen, the suspension was thawed again at 37° C. and, after another wash, incubated at 37° C. for 15 minutes. The protein material was subsequently washed four times by centrifugation and suspension and was stored at –70° C. until used.

For the binding assay, the protein material thawed at 37° C. was washed twice by centrifugation at 48,000 g (20 minutes) and subsequent suspension in a buffer solution B' composed of 50 mM TRIS-Hcl, pH 7.4. Subsequently 0.15 mg of membrane material, 0.3 μCi of $^3$H-5,7-dichlorokynurenic acid (16 Ci/mmol) and compound I were dissolved in 1 ml of buffer solution B' and incubated on ice for 30 minutes. The incubated solution was centrifuged at 150,000 g for 2 minutes. After removal of the supernatant liquid, the pellets were suspended twice in 1.5 ml of cold buffer solution B' each time. After measurement of the radioactivity of the $^3$H-5,7-dichlorokynurenic acid bound to the membranes in the pellet, the $K_I$ was found by regression analysis of the displacement plots.

The results of this experiment were as follows:

| Substance of Example No. | Binding of dichlorokynurenic acid $K_I$ [μm] |
|---|---|
| 2 | 0.2 |
| 3 | 1.2 |
| 6 | 1.6 |
| 7 | 0.4 |
| 8 | 0.2 |
| 9 | 0.65 |
| 10 | 0.3 |
| 11 | 0.1 |
| 12 | 1.6 |
| 15 | 2.0 |
| 18 | 0.8 |
| 21 | 2.6 |

The pharmaceutical compositions are produced in a conventional way, eg. by mixing the agent with the conventional excipients and diluents.

The pharmaceutical compositions can be administered in various ways, such as orally, parenterally, subcutaneously, intraperitonally and topically. Thus, possible presentations are tablets, emulsions, solutions for infusion and injection, pastes, ointments, gels, creams, lotions, dusting powders and sprays.

The pharmaceutical compositions according to the invention contain a therapeutically effective amount of the compounds I in addition to conventional pharmaceutical ancillary substances. For local external use, eg. in dusting powders and ointments, the agents can be present in the conventional concentrations. As a rule, the agents are present in an amount of from 0.001 to 5% by weight, preferably 0.01 to 0.5% by weight.

On internal use, the preparations are administered in single doses. 0.1 to 50 mg, preferably 0.1 to 10 mg, of agent per kg of body weight are given in a single dose. The compositions can be administered in one or more dosages each day depending on the nature and severity of the disorders. The daily dose is, as a rule, from 0.1 to 100 mg per kg of body weight on oral administration and from 0.01 to 10 mg per body weight on parenteral administration.

The pharmaceutical compositions according to the invention contain, appropriate for the desired mode of administration, the conventional excipients and diluents in addition to the agent.

For local external use it is possible to use pharmaceutical ancillary substances such as ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and wool fat. Examples suitable for internal use are lactose, propylene glycol, ethanol, starch, talc and polyvinylpyrrolidone.

It is furthermore possible for antioxidants such as tocopherol and butylated hydroxyanisole as well as butylated hydroxytoluene, flavor-improving additives, stabilizers, emulsifiers and bleaches to be present.

The substances which are present in the composition besides the agent, as well as the substances used for producing the pharmaceutical composition must be toxiocologically acceptable and compatible with the particular agent.

EXAMPLES

I. Synthesis of some intermediates

A 2-Chloro-4-hydrazino-7,8,9,10-tetrahydroquinazoline 113 g of 2,4-dichloro-7,8,9,10-tetrahydroquinazoline were dissolved in 1 liter of methylene chloride and, at 20° C., 113 ml of hydrazine hydrate were added. The solution was stirred overnight, the solvent was removed by distillation, and the residue was stirred with water, dried and treated with methyl tert-butyl ether. Yield: 90.2 g.

B 2-Chloro-4-N(N'-ethyloxalylhydrazino)-7,8,9,10-tetrahydroquinazoline 1.5 g of Example A in 50 ml of $CH_2Cl_2$ are mixed with 1.2 ml of triethylamine and 1.2 g of ethyl oxalyl chloride. The mixture is stirred at room temperature overnight, the solvent is stripped off, the residue is stirred with water and dried. Yield: 1.8 g.

II. Synthesis of compounds according to the invention

Example 1

Ethyl 7,8,9,10-tetrahydro-1,2,4-triazolo[1,5-c]quinazolin-5-one-2-carboxylate 35 g of 2-chloro-4-N-(N'-ethyloxalylhydrazino)-7,8,9,10-tetrahydroquinazoline were refluxed in 250 ml of acetic acid for 2.5 h. The solvent was removed by distillation and the residue was stirred with MTB, filtered off with suction and dried.

Yield: 25.5 g. Melting point 266°–268° C.

Example 2

7,8,9,10-Tetrahydro-1,2,4-triazolo[1,5-c]quinazolin-5-one-2-carboxylic acid 5 g of ester from Example 1 were stirred in 120 ml of 1N NaOH at room temperature for 4 h. The solution was extracted with MTB and acidified, and the precipitate was filtered off with suction, washed with water and dried. Yield: 3.2 g. Melting point 188° C.

Example 3

7,8,9,10-Tetrahydro-1,2,4-triazolo[1,5-c]quinazolin-5-one-2-carboxylic acid N-benzylolylamide.

1.4 g of acid from Example 2 in 20 ml of methylene chloride were mixed with 0.75 g of N-hydroxysuccinimide and 1.25 g of dicyclohexylcarbodiimide. The mixture was stirred at room temperature overnight, and the solid was filtered off with suction, thoroughly washed with methylene chloride and resuspended in 50 ml of methylene chloride. Subsequently 0.63 g of benzylamine was added, the mixture was stirred at room temperature overnight, and the solid was filtered off with suction and extracted with hot ethanol. Yield: 0.9 g.

Melting point 255°–259° C.

The following compounds of the formula I were prepared in a similar way to Examples 1–3:

| Example No. | D | A—X | Melting point (°C.) |
|---|---|---|---|
| 4 |  | CO₂— | 232–236 |
| 5 |  | CO₂—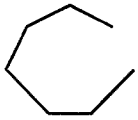 | 262–265 |
| 6 |  | CO₂H | 270–272 |
| 7 | 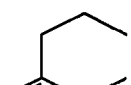 | CO₂C₂H₅ | 242–243 |
| 8 | 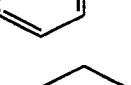 | CO₂H | 182–187 |
| 9 | 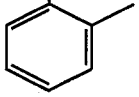 | CO₂C₂H₅ | 278–280 |
| 10 |  | CO₂H | 251–255 |
| 11 |  | C₂H₄COOH | 304–308 |
| 12 |  | CONH—(3,4-Cl₂) | 286–288 |
| 13 |  | CONH—(OCH₃) | 262–268 |
| 14 |  | CONH—(CH₃) | 285–290 |
| 15 |  | CONH—(NO₂) | 273–280 |

| | | | |
|---|---|---|---|
| 16 |  | CO₂C₂H₅ | 190–193 |
| 17 |  | CO₂C₂H₅ | 216–221 |
| 18 |  | CO₂H | 196–202 |
| 19 |  | CO₂C₂H₅ | 262–270 |
| 20 |  | CONH–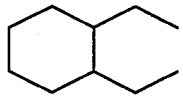 | 285–288 |
| 21 | 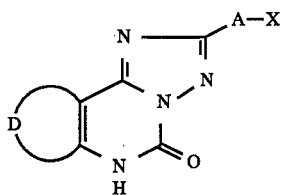 | CO₂C₂H₅ | 221–226 |

We claim:

1. A triazolpyrimidone of the formula I

where

A is a direct linkage or a $C_{1-3}$-alkylene chain,

D is a $C_{3-6}$-alkylene chain which can be interrupted by a sulfur atom can carry a fused benzene or cyclohepane ring, X is a carboxyl group which may be in the form of its salt with a physiologically tolerated amine cation or metal cation; the radical $$-\underset{\underset{O}{\|}}{C}-OR^4,$$

where $R^4$ is a $C_{1-8}$-alkyl radical.

2. A triazolpyrimidone of the formula I as defined in claim 1, wherein D is an unsubstituted $C_3$–$C_6$-alkylene chain.

3. A triazolpyrimidone of the formula I as defined in claim 1, wherein D is an unsubstituted $C_3$-chain and A—X is $CO_2H$.

4. The triazolpyrimidone of the formula I as defined in claim 1 which is ethyl 7,8,9,10-tetrahydro-1,2,4-triazolo(1,5-c)quinazolin-5-one-2-carboxylate.

5. The triazolpyrimidone of the formula I as defined in claim 1 which is 7,8,9,10-tetrahydro-1,2,4-triazolo(1,5-c)quinazolin-5-one-2-carboxylic acid.

6. A method for treating ischemic cerebral insults which comprises administering to patients in need of such treatment an effective dose of the substance of the formula I as defined in claim 1.

* * * * *

UNITED STATES PATENT AND TRADEMARK OFFICE
CERTIFICATE OF CORRECTION

PATENT NO.: 5,654,310

DATED: August 5, 1997

INVENTOR(S): SCHLECKER et al.

It is certified that error appears in the above-identified patent and that said Letters Patent is hereby corrected as shown below:

Column 11, claim 1, line 46, between "atom" and "can", insert --or--.

Column 11, claim 1, line 46, "cyclohepane" should read --cyclohexane--.

Signed and Sealed this

Twenty-third Day of September, 1997

Attest:

BRUCE LEHMAN

Attesting Officer    Commissioner of Patents and Trademarks